(12) United States Patent
Schubert

(10) Patent No.: US 6,875,579 B1
(45) Date of Patent: Apr. 5, 2005

(54) DEVICE FOR BINDING MOLECULES, MOLECULAR GROUPS, MOLECULAR PARTS AND/OR CELLS

(76) Inventor: Walter Schubert, Am Mühlengrund 9, D-39175 Biederitz (DE)

(*) Notice: Subject to any disclaimer, the term of this patent is extended or adjusted under 35 U.S.C. 154(b) by 0 days.

(21) Appl. No.: 09/613,964

(22) Filed: Jul. 11, 2000

(30) Foreign Application Priority Data

Jul. 14, 1999 (DE) .......................................... 199 32 958

(51) Int. Cl.[7] .......................... G01N 33/53; G01N 33/543
(52) U.S. Cl. .......................... 435/7.21; 435/4; 435/7.23; 435/283.1; 435/287.1; 435/287.3; 435/287.6; 435/288.4; 435/288.5; 422/50; 422/68.1; 422/100; 422/243; 436/174; 436/180; 436/807
(58) Field of Search ........................ 435/4, 7.21, 7.23, 435/283.1, 287.1, 287.3, 0.6, 288.4, 0.5, 287.6, 288.5; 436/807, 174, 180; 422/50, 68.1, 100, 243

(56) References Cited

U.S. PATENT DOCUMENTS

| | | | | |
|---|---|---|---|---|
| 5,716,825 A | * | 2/1998 | Hancock et al. | ......... 435/286.5 |
| 5,772,966 A | * | 6/1998 | Maracas et al. | ............ 422/100 |
| 5,882,903 A | * | 3/1999 | Andrevski et al. | ............ 422/50 |
| 5,925,511 A | * | 7/1999 | Fuhr et al. | ..................... 435/1.3 |
| 5,958,760 A | * | 9/1999 | Freeman | ...................... 356/398 |
| 5,960,640 A | * | 10/1999 | Teppke | ......................... 62/320 |
| 6,150,173 A | * | 11/2000 | Schubert | ..................... 422/100 |
| 6,366,924 B1 | * | 4/2002 | Parce | ...................... 707/104.1 |

FOREIGN PATENT DOCUMENTS

| | | | | |
|---|---|---|---|---|
| DE | 2641097 | | 5/1978 | .......... G01N/33/16 |
| DE | 224119 A1 | | 11/1983 | ........... G01N/1/28 |
| DE | 3635013 | | 5/1988 | ........... G01N/1/28 |
| DE | 3134611 | | 2/1990 | .......... G01N/21/07 |
| DE | 19643921 | | 2/1998 | ........... C12M/1/38 |
| GB | 2122369 A | | 1/1984 | ........... G01N/1/28 |

* cited by examiner

*Primary Examiner*—Long V. Le
*Assistant Examiner*—Kartic Padmanabhan
(74) *Attorney, Agent, or Firm*—Womble Carlyle Sandridge & Rice, PLLC

(57) ABSTRACT

The present invention relates to a device for binding molecules, molecular groups, molecular parts and/or cells contained in a liquid to target structures, the device having at least one object holder with at least one target structure firmly held therein and which contacts at least one duct made of at least one material. One aperture of the duct is a liquid inlet aperture, and a second aperture is a liquid outlet aperture. At least one object holder thermostat is used for cooling the object holder.

8 Claims, 2 Drawing Sheets

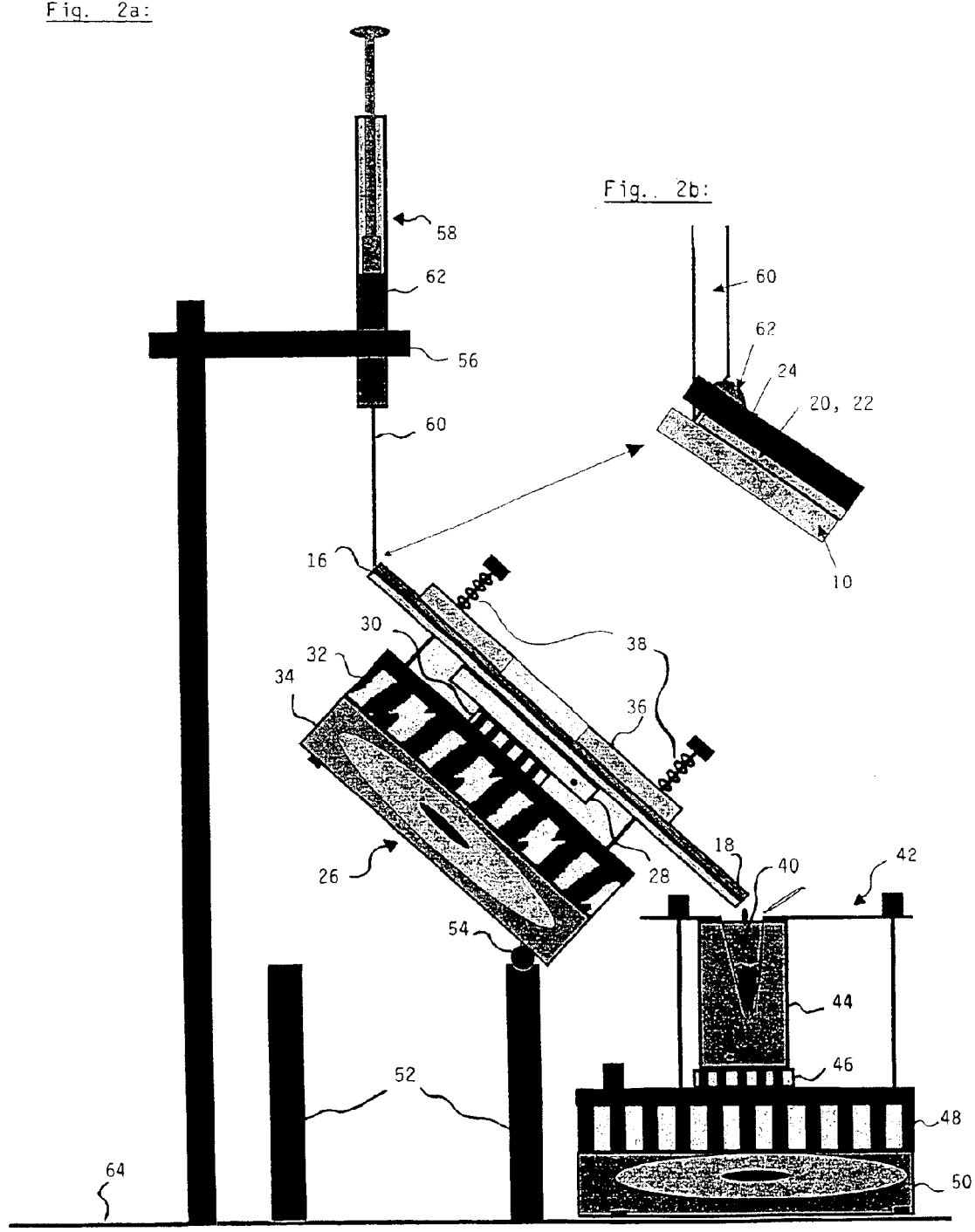

DEVICE FOR BINDING MOLECULES, MOLECULAR GROUPS, MOLECULAR PARTS AND/OR CELLS

CROSS-REFERENCE TO RELATED APPLICATIONS

This application claims the benefit of German Patent Application No. 19932958.3, filed on Jul. 14, 1999.

BACKGROUND OF THE INVENTION

The present invention relates to a device for binding molecules, molecular groups, molecular parts and/or cells contained in a liquid to target structures, as well as to a method for binding molecules, molecular groups, molecular parts and/or cells contained in a liquid to target structures.

The only method known so far for binding molecules, molecular groups, molecular parts and/or cells contained in a liquid to target structures is the one according to "Stamper and Woodruff (1976) J. Exp. Med 144, 828–833". This method comprises the fixing of target structures to a surface and subsequently rehydrating them. Then, the target structures are coated with 100 to 200 $\mu l$ of the liquid containing the molecules, groups of molecules, parts of molecules and/or cells. Incubation (e.g.: 30 min, 7° C.) thereof on a shaker or rotating table is followed by a rinsing step which will remove any non-binding matter.

One major disadvantage of this method is the fact that it is performed manually. Moreover, motion devices are used for obtaining the binding equilibrium which only poorly simulate the conditions prevailing in certain natural systems. Another shortcoming is that the rinsing step may destroy the often weak adherence of ingredients of the liquid to the target structures. Yet another disadvantage of this method is that it is not capable of stopping metabolic processes.

It is therefore the object of the present invention to provide a device and a method for simulating the short-term interactions occurring between molecules, molecular groups, molecular parts and/or cells in a liquid, on the one hand, and the target structures, on the other, at the same time allowing most of the metabolic processes to be stopped at any time.

This object is accomplished by a device and a method having the features of the independent claims.

Advantageous embodiments are described in the sub-claims.

A device of the invention for binding molecules, molecular groups, molecular parts and/or cells contained in a liquid to target structures comprises at least one object holder with at least one target structure firmly held therein which is in contact with at least one duct made of at least one material, said duct including, at its one aperture, a liquid inlet and, at its other aperture, a liquid outlet, as well as at least one object holder thermostat used for cooling the respective object holder.

This is based on the inventive idea that flowing a liquid containing molecules, molecular groups, molecular parts and/or cells through a duct which is in contact with a target structure will cause said molecules, molecular groups, molecular parts and/or cells to bind to said target structure. Any non-binding matter can be removed via the second duct aperture. At the same time, the temperature of the object holder will be controlled by the object holder thermostat. Owing to the flowing motion, passing the liquid containing molecules, molecular groups, molecular parts and/or cells over the target structure is a better way of simulating natural systems with short-term interactions than by means of a prior art shaker or a prior art rotating table. A particular advantage of the invention is that it allows an interruption of metabolic processes at any time by decreasing the temperature of the object holder by means of the object holder thermostat. In doing so, the temperature of the object holder will be 2–10° C., in particular 4° C.

In an advantageous embodiment of the invention, the duct is formed by the object holder and paraffin-like sheet material. This allows the duct to widen, if necessary, preventing excessive pressure build-up within said duct.

In yet another advantageous embodiment of the invention, the discharged liquid will be collected in a vessel, thus preventing a loss of liquid which has already passed the duct, which liquid may be difficult and/or expensive to prepare.

In another advantageous embodiment of the invention, the temperature of the vessel will be cooled by a vessel thermostat, thus preventing any metabolic processes from occurring within said vessel and allowing the liquid or its ingredients to be used again.

A method of the invention for binding molecules, molecular groups, molecular parts and/or cells contained in a liquid to target structures comprises the following steps: (a) passing liquid through a duct and over an object holder carrying a target structure firmly held therein, (b) removing any non-binding matter via a second duct aperture and collecting such matter in a vessel, (c) cooling said object holder by means of an object holder thermostat, and (d) fixing the molecules, molecular groups, molecular parts and/or cells adhering to the object holder.

In yet another advantageous embodiment of the invention, the device is used in an automated method for determining molecular classes, molecular groups, molecular parts in a solid or liquid object according to U.S. patent application Ser. No. 09/353,942, the entire specification of which is incorporated herein by this reference. This will allow identification and characterization of the binding partners. It will be possible at the same time to identify and characterize the molecular classes, molecular groups and/or molecular parts required for the binding process. Such application will be advantageous in numerous areas of chemistry, biology, biochemistry and especially medicine. This will not only open up new possible ways of diagnosing, but will also provide a new test system for therapeutic approaches on a molecular level.

BRIEF DESCRIPTION OF THE DRAWINGS

Further details, features and advantages of the invention will ensue from the description, which follows, of an embodiment illustrated in the drawings, of which:

FIG. 1b is a cross-sectional view of the object holder of FIG. 1a;

FIG. 2a is a schematic lateral view of the device of the invention; and

FIG. 2b is a detailed view of an element of the device of the invention.

DETAILED DESCRIPTION OF THE INVENTION

Figure 1A:
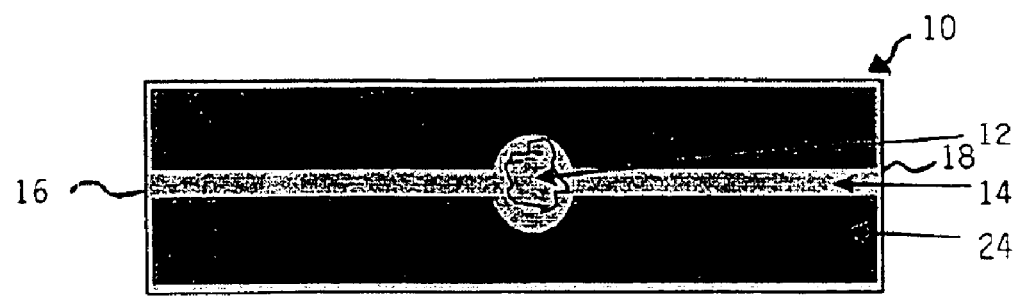
FIG. 1a is a top view of an object holder of the device of the invention.
Figure 1B:
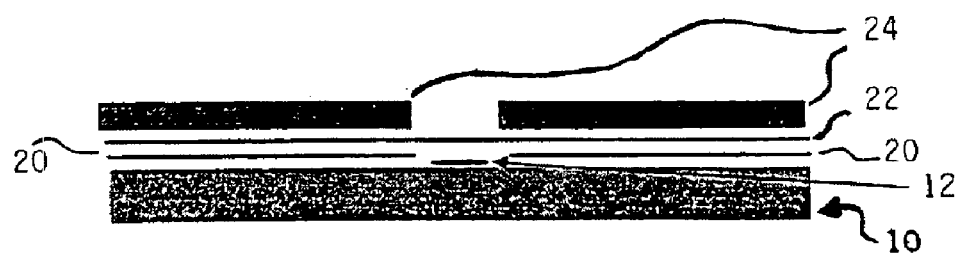

FIG. 1a is a top view of an object holder 10 of the device for binding molecules, molecular groups, molecular parts and/or cells, whereas FIG. 1b is a cross-sectional view of the object holder 10.

It can be seen that a target structure 12 has been detachably mounted on said object holder 10 and contacts a duct 14 defined by said object holder 10, two paraffin-sheet strips 20 and a continuous paraffin-sheet layer 22. Two aluminum rails 24 are mounted on said paraffin-sheet layer 22 whose surface areas are is similar to that of said paraffin-sheet strips 20 underneath them. Furthermore, it may be gathered from this figure that duct 14 has first and second duct apertures 16, 18 for inlet and outlet, resp., of liquid 62. Liquid 62 may be discharged by means of a plunger mechanism 58, a pump (not shown), or under the influence of gravity and by means of a pump (not shown), or under the influence of gravity alone.

FIG. 2a is a schematic lateral view of the device for binding molecules, molecular groups, molecular parts and/or cells, with said object holder 10, including paraffin-sheet strips 20, paraffin-sheet layer 22, aluminum rails 24, a hollow needle 60 and said liquid 62, being additionally shown in detail in FIG. 2b.

These illustrations show that—besides the elements mentioned above—the device includes an object holder thermostat 26 comprising a cooling plate 28, made of aluminum, a first Peltier element 30, a first cooling element 32 and a first fan 34. Said device is mounted on a post 52 with clamping joint 54 in such a way that the angle between the mounted object holder 10 and a basic plate 64 is approx. 20–70°. Object holder 10 is firmly pressed onto object holder thermostat 26 by a pressure plate with a central aperture 36 which rests on aluminum rails 24. Sufficient pressure is ensured by way of springs 38.

Liquid 62 is introduced into the first duct aperture 16 by means of a suture 58 detachably mounted by means of a suture support 56, and a hollow needle. Under the influence of gravity, liquid 62 will thus flow through duct 14 and contact target structure 12, allowing the desired and predetermined ingredients of liquid 62 to bind to target structure 12. Finally, liquid 62 will reach the second duct aperture 18, exit duct 14 and drip into a vessel 40 surrounded by a vessel thermostat 42. Said vessel thermostat 42 comprises a vessel support 44, made of copper, a second Peltier element 46, a second cooling element 48 and a second fan 50.

Once all of said liquid 62 (approx. 1 ml) has passed through said duct 14, object holder thermostat 26 and vessel thermostat 42 will cool said vessel 40 and said object holder 10 down to 4° C. so as to stop any metabolic activity.

Liquid 62 may contain lymphocytes. Target structure 12 is a tissue section or a membrane coated with molecules or molecular combinations.

What is claimed is:

1. A device for delivering a liquid to a target structure, wherein the device comprises:

a) an object holder thermostat;

b) an object holder, wherein said object holder is operably in contact with said object holder thermostat;

c) a stretchable sheet disposed between said object holder and at least one rail;

d) at least one strip disposed between said object holder and said stretchable sheet; and e) a duct, wherein said duct is defined by at least said object holder, said strip and said stretchable sheet, wherein said at least one rail is mounted on said stretchable sheet thereby cooperating with at least the stretchable sheet and the object holder to define the geometry of said duct, and wherein said duct has a liquid inlet and a liquid outlet.

2. The device of claim 1, is further comprising a means for delivering a liquid to said duct, said means for delivering being selected from a plunger mechanism and a pump.

3. The device of claim 1, wherein said liquid outlet is operably connected to a discharge pump.

4. The device of claim 1, wherein said object holder thermostat comprises a Peltier element.

5. The device of claim 1, further comprising a vessel disposed to receive a liquid from said liquid outlet.

6. The device of claim 5, wherein said vessel is operably contacted with a vessel thermostat.

7. The device of claim 6, wherein said vessel thermostat comprises a Peltier element.

8. The device of claim 1, where said at least one strip comprises at least one stretchable strip disposed between said object bolder and said stretchable sheet.

* * * * *